(12) United States Patent
Zeiner et al.

(10) Patent No.: US 9,102,936 B2
(45) Date of Patent: Aug. 11, 2015

(54) METHOD OF ADAPTOR-DIMER SUBTRACTION USING A CRISPR CAS6 PROTEIN

(71) Applicant: Agilent Technologies, Inc., Loveland, CO (US)

(72) Inventors: Gusti Zeiner, Loveland, CO (US); Laurakay Bruhn, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 86 days.

(21) Appl. No.: 13/894,878

(22) Filed: May 15, 2013

(65) Prior Publication Data

US 2013/0330778 A1 Dec. 12, 2013

Related U.S. Application Data (60) Provisional application No. 61/658,176, filed on Jun. 11, 2012.

(51) Int. Cl.
| | | |
|---|---|---|
| *C07H 21/02* | (2006.01) | |
| *C07H 21/04* | (2006.01) | |
| *A61K 48/00* | (2006.01) | |
| *C12N 15/10* | (2006.01) | |

(52) U.S. Cl.
CPC .................................. *C12N 15/1096* (2013.01)

(58) Field of Classification Search
CPC ............................... C12N 15/113; A61K 48/00
See application file for complete search history.

(56) References Cited

U.S. PATENT DOCUMENTS

| 2010/0167954 A1 | 7/2010 | Earnshaw et al. |
| 2011/0217739 A1 | 9/2011 | Terns et al. |
| 2011/0319290 A1 | 12/2011 | Raymond et al. |
| 2012/0108440 A1 | 5/2012 | Lau et al. |

FOREIGN PATENT DOCUMENTS

| WO | WO2011143124 | 11/2011 |
| WO | WO2012033667 | 3/2012 |

OTHER PUBLICATIONS

Sternberg, et al., Mechanism of substrate selection by a highly specific CRISPR endoribonuclease. RNA Society, 2012, 18:1-12.
Wang, et al., Interaction of the Cas6 Riboendonuclease with CRISPR RNAs: Recognition and Cleavage. Structure, 2011, 19:257-64.

*Primary Examiner* — Amy Bowman (57) ABSTRACT

A method of processing a target RNA is provided. In certain embodiments, this method comprises: contacting the products of an RNA ligase-mediated ligation reaction with an CAS6 protein, wherein: (i) the RNA ligase-mediated ligation reaction comprises: a target RNA, an RNA ligase, and first and second adaptors that can ligate together to produce an adaptor dimer that contains a CRISPR stem loop; and (ii) the CAS6 protein recognizes the CRISPR stem loop; thereby preventing the adaptor dimer from being reverse transcribed.

16 Claims, 2 Drawing Sheets

METHOD OF ADAPTOR-DIMER SUBTRACTION USING A CRISPR CAS6 PROTEIN

CROSS-REFERENCING

This application claims the benefit of U.S. provisional application Ser. No. 61/658,176, filed Jun. 11, 2012, which application is incorporated by reference in its entirety.

INTRODUCTION

In some cDNA synthesis methods, adaptors are ligated to RNA, and cDNA synthesis of the RNA is primed using one of the ligated adaptors. However, in certain cases, the initial ligation step can produce so-called "adaptor-dimers" (i.e., a product made by the direct ligation of one adaptor molecule to another, rather than to a target RNA). Without their removal, such adaptor dimers can in certain instances dramatically decrease the efficiency of future steps.

BRIEF DESCRIPTION OF THE FIGURES

The skilled artisan will understand that the drawings, described below, are for illustration purposes only. The drawings are not intended to limit the scope of the present teachings in any way.

DEFINITIONS

Before describing exemplary embodiments in greater detail, the following definitions are set forth to illustrate and define the meaning and scope of the terms used in the description.

The term "RNA sample", as used herein, relates to a mixture of materials, typically, although not necessarily, in liquid form, containing one or more RNA molecules. An RNA sample may be obtained from cells, e.g., mammalian cells, for example. An RNA sample may contain a population of different RNA molecules, in which case it may contain more than 1,000, more than 10,000, more than 50,000, or more than 100,000 up to 1M or more different species of RNA, i.e., RNA molecules of different sequence. An RNA sample may contain long RNA molecules, fragments of long RNA molecules and/or short RNA molecules, as defined below.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine and thymine (G, C, A and T, respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers. Oligonucleotides may be 5 to 20, 11 to 30, 31 to 40, 41 to 50, 51-60, 61 to 70, 71 to 80, 80 to 100, 100 to 150 or 150 to 200, up to 500 nucleotides in length, for example.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "hybridization conditions" as used herein refers to hybridization conditions that are sufficient to anneal an oligonucleotide of a sufficient length to a probe that is complementary to a nucleotide sequence of the probe. The hybridization conditions provide for dissociation of duplexes that anneal over a short length of region (e.g. less than 50, less than 40, less than 30, or less than 20 contiguous nucleotides). Such conditions may differ from one experiment to the next depending on the length and the nucleotide content of the complementary region. In certain cases, the temperature for low-stringency hybridization may be 5°-10° C. lower than the calculated Tm of the resulting duplex under the conditions used.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term stringent assay conditions refers to the combination of hybridization and wash conditions.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

As used herein, the term "data" refers to refers to a collection of organized information, generally derived from results of experiments in lab or in silico, other data available to one of skilled in the art, or a set of premises. Data may be in the form of numbers, words, annotations, or images, as measurements or observations of a set of variables. Data can be stored in various forms of electronic media as well as obtained from auxiliary databases.

If a nucleic acid probe "corresponds to" or is "for" a certain RNA, the nucleic acid probe base pairs with, i.e., specifically hybridizes to, that RNA. As will be discussed in greater detail below, a nucleic acid probe for a particular RNA and the particular RNA, or complement thereof, contains at least one region of contiguous nucleotides that is identical in sequence.

As used herein, the term "total cellular RNA" is an RNA sample that contains at least tRNA, rRNA, mRNA, lincRNA and small RNA.

As used herein, the term "depleted", in the context of a total cellular RNA sample that has been depleted for tRNA, rRNA, or another type of RNA, is total cellular RNA sample from which tRNA, rRNA, or another type of RNA has been subtracted, i.e., removed.

As used herein, the term "initial RNA sample" is an RNA sample that has not been exposed to fragmentation conditions and that contains intact RNA molecules. Such a sample may contain, for example, total cellular RNA or a total cellular RNA that has been depleted for rRNA and/or tRNA, or another type of RNA. An initial RNA sample can contain at least one type of intact long RNA and one type of short RNA.

As used herein, the term "fragmented RNA sample" is a sample that contains fragments of RNA. A fragmented RNA sample can made from an initial RNA sample by exposing the initial RNA sample to fragmentation conditions. Fragmented RNA samples include RNA that has been extracted from a formalin-fixed paraffin embedded tissue (FPET) sample.

As used herein, the term "long RNA molecules" refers to RNA molecules that are at least 50 nt in length. Long RNA molecules include mRNA molecules, rRNA molecules, tRNA molecules, pre-miRNAs, snRNAs and long non-coding RNA molecules such as large intergenic RNA (lincRNA) molecules. Some long RNA molecules may be in the range of 50 nt to 10 kb in length, e.g., 200 nt to 10 kb in length.

As used herein, the term "short RNA molecules" refers to RNA molecules that are below 50 nt in length. Short RNA molecules include a variety of small non-coding regulatory RNAs generically referred herein to as "small RNAs", i.e, short interfering RNAs, microRNAs, tiny non-coding RNAs piwi-interacting small RNAs (piRNAs) and small modulatory RNAs.

As used herein, the term "fragments of long RNA molecules" refer to RNA fragments that are obtained by fragmentation of long RNA molecules. Depending on how fragmentation is done, fragments of long RNA molecules may have a 5'OH group and a 2',3' cyclic phosphate group at the 3' terminus.

As used herein, the term "fragmentation conditions" refer to an environment or an agent that induces non-sequence specific fragmentation of long RNA molecules. As will be described in greater detail below, when fragmenting a sample containing both long RNA molecules and short RNA molecules, the fragmentation conditions can be tailored to provide for fragmentation of long RNA molecules without significant fragmentation of short RNA molecules.

As used herein, the term "adaptor" refers to an oligonucleotide that may be composed of any type of nucleotide. An adaptor may be, e.g., an RNA adaptor, a DNA adaptor, or it may be composed of both ribonucleotides and deoxyribonucleotides or analogs thereof. An adaptor may be labeled or unlabeled and in certain cases may be of 5-50 bases, e.g., 6 to 12 bases, in length or longer depending on the application.

As used herein, the terms "5'-OH" and "5'-hydroxyl" refers to a nucleotide at the 5' terminus of a nucleic acid, where the nucleotide has a hydroxyl group at the 5' position.

As used herein, the terms "3'-OH" and "3'-hydroxyl" refers to a nucleotide at the 3' terminus of a nucleic acid, where the nucleotide has a hydroxyl group at the 3' position.

As used herein, the term "3'-P" or "3'-phosphate" refers to a nucleotide at the 3' terminus of a nucleic acid, where the nucleotide has a phosphate group at the 3' position.

As used herein, the term "5'-P" or "5'-phosphate" refers to a nucleotide at the 5' terminus of a nucleic acid, where the nucleotide has a phosphate group at the 5' position.

As used herein, the terms "2'-PO and 3'-OH" and "2'-phosphate and 3'-hydroxyl", in the context of a 3' terminus, refers to a nucleotide at the 3' terminus of a nucleic acid, where the sugar moiety of the nucleotide has both a phosphate group at the 2' position and a hydroxyl group at the 3' position.

As used herein, the term "2',3'-cyclic phosphate", in the context of a 3' terminus comprising 2',3'-cyclic phosphate, refers to a nucleotide at the 3' terminus of a nucleic acid, where the sugar moiety of the nucleotide has a phosphate group connected to the 2' and 3' positions, as shown below:

As used herein, the term "eukaryotic tRNA ligase" refers to a multifunctional enzyme that has: a) a ligase activity that catalyzes ligation of the 5' terminus of a nucleic acid having a 5'-phosphate to the 3' terminus of a nucleic acid having a 3' terminus having a 2'-phosphate and a 3'-hydroxyl to produce a ligation product that contains a 2' phosphate at the site of ligation; and, optionally b) a cyclic phosphodiesterase (CPD) activity that catalyzes the hydrolysis of a 2',3'-cyclic phosphate group to produce a 2'-phosphate and 3'-hydroxyl; and/or c) a kinase activity that catalyzes the phosphorylation of a 5'-hydroxyl to produce a 5'-phosphate. Wild type tRNA ligase enzymes have all three activities and are arranged as follows: a N-terminal ligase module, a central kinase module and a C-terminal 2'3'-cyclic phosphodiesterase module. Such enzymes have been identified and characterized in yeast and plants, and are expected to be present in a number of other eukaryotes, e.g., mammals and archebacteria (see, e.g., Ramirez RNA 2008 14: 1737-45; Englert Nuc. Acids Res. 2005 33: 388-399; Sawaya J. Biol. Chem. 2003 278: 43928-43928; Apostol J. Biol. Chem. 1991 266: 7445-7455; Phizicky J. Biol. Chem. 1986 261: 2978-2986; Nandakumar Mol. Cell. 2008 31: 278-286; Sugahara RNA 2007 13: 671-681; and Schutz RNA 2010 16: 621-631). As will be described in greater detail below, a eukaryotic tRNA ligase employed in a subject method may only have the ligase activity and, optionally, the kinase and/or cyclic phosphodiesterase activity. Thus, in particular cases, the eukaryotic tRNA ligase used in the method may minimally have a ligase domain having an amino acid sequence that is at least 80% to the amino acid of the ligase domain of a wild type eukaryotic tRNA ligase. The ligase domain is sufficient to catalyze ligation of the 5' terminus of a nucleic acid having a 5'-phosphate to the 3' terminus of a nucleic acid having a 3' terminus having a 2'-phosphate and a 3'-hydroxyl to produce a ligation product that contains a 2' phosphate at the site of ligation. The 2'-phosphate group may be removed by a 2'-phosphate group-specific specific phosphotransferase in the presence of $NAD^+$, or with a non-specific alkaline phosphatase, if necessary (Culver J. Biol. Chem. 1997: 13203-13210; Schutz RNA 2010 16: 621-631).

As used herein, the term "RtcB ligase" refers to any enzyme that has the ability to catalyze the ligation of the 3' end of an RNA having a 3' terminal 2'3'-cyclic phosphate to the 5' end of an RNA having a 5'-hydroxyl. Several examples of such enzymes (which are generically but not always referred to as "RtcB" protein in the art), are known in bacteria, archaea and eukarya (particularly in metazoan and protozoa species but not in some fungi and plants). RtcB ligases are structurally unrelated to 3'-OH RNA ligases, which ligate a 5'-phosphate-containing RNA to a 3'-hydroxyl-containing RNA, rather than ligating a 5'-hydroxyl-containing RNA to a 3' terminal 2',3'-cyclic phosphate-containing RNA. The structure, function, biochemical features and phylogenetic distribution of various RtcB ligases are described in a variety of publications, including: Tanaka et al (*RtcB is the RNA ligase component of an Escherichia coli RNA repair operon*. J. Biol. Chem. Jan. 11, 2011, e-pub ahead of print), Englert et al (*Archaeal 3'-phosphate RNA splicing ligase characterization identifies the missing component in tRNA maturation*. Proc. Natl. Acad. Sci. 2011 108: 2-7), and Okada et al (*Crystal structure of an RtcB homolog protein (PH1602-extein protein) from Pyrococcus horikoshii reveals a novel fold*. Proteins 2006 63: 1084-6)

As used herein, the term "3'-OH RNA ligase" refers to an enzyme that catalyzes the ligation of the 3' end of an RNA containing a 3'-hydroxyl to the 5' end of an RNA containing a 5'-phosphate in an ATP-dependent reaction. Many examples of these enzymes are known. 3'-OH RNA ligases may be derived from bacteriophage, or from their prokaryotic hosts, for example. T4 RNA ligase is one example of a 3'-OH RNA ligase (see, e.g., Wood et al, Mol. Cell. 2004 13: 455-6), and others are known (e.g., Torchia et al (*Archaeal RNA ligase is a homodimeric protein that catalyzes intramolecular ligation of single-stranded RNA and DNA*. Nucl. Acids Res. 2008 36: 6218-6227).

As used herein, the term "adaptor dimer" refers to a product produced by two adaptors ligating directly together.

As used herein, the term "CAS6 protein" refers to any wild type protein or variant thereof that binds to a CRISPR stem loop. Wild type CAS6 proteins and corresponding CRISPR stem loops are part of the CRISPR-CAS adaptive immune system found in many bacteria and archae. The CRISPR-CAS system is reviewed in a number of publications, including Sternberg et al (Mechanism of substrate selection by a highly specific CRISPR endoribonuclease RNA 2012 18: 661-72), Makarova et al (Unification of Cas protein families and a simple scenario for the origin and evolution of CRISPR-Cas systems Biol Direct. 2011 6: 38), Deltcheva et al (CRISPR RNA maturation by trans-encoded small RNA and host factor RNase III) Nature 2011 471: 602-7, Wang et al (Interaction of the Cas6 riboendonuclease with CRISPR RNAs: recognition and cleavage Structure 2011 19: 257-64), Carte et al (Binding and cleavage of CRISPR RNA by Cas6 RNA 2010 16: 2181-8), Carte et al (Cas6 is an endoribonuclease that generates guide RNAs for invader defense in prokaryotes Genes Dev. 2008 22: 3489-96), and Haurwitz et al (Science. 2010 329: 1355-8 Sequence- and structure-specific RNA processing by a CRISPR endonuclease), which are incorporated by reference. A CAS6 protein may be catalytically active in that it catalyzes the cleavage of a CRISPR stem loop. Certain embodiments of the method may employ a CAS6 protein that is not catalytically active.

As used herein, the terms "CRISPR stem loop" and "CRISPR hairpin" refer to the RNA structure to which a CAS6 endonuclease binds. The sequence of a wild type CRISPR stem loop may vary from species to species. The sequence of a CRISPR stem loop used in the subject method may differ from a wild-type sequence by one or two nucleotides and still be recognized by a CAS6 protein. In many genomes, a CRISPR sequence (from which a CRISPR stem loop is derived) is composed of 25-50 bp repeats separated by unique sequence spacers of similar length.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Methods

A method of processing a target RNA is provided. In certain embodiments, this method comprises: contacting the products of an RNA ligase-mediated ligation reaction with an CAS6 protein, wherein: (i) the RNA ligase-mediated ligation reaction comprises: a target RNA, an RNA ligase, and first and second adaptors that can ligate together to produce an adaptor dimer that contains a CRISPR stem loop; and (ii) the CAS6 protein recognizes the CRISPR RNA stem-loop. Treatment of the ligation reaction with the CAS6 protein prevents the adaptor dimer from being reverse transcribed. In certain cases, the method may involve: a) combining the first and second adaptors with a target RNA and an RNA ligase to produce a ligation product that includes adaptor-ligated target RNA and adaptor dimers, and b) contacting the ligation product with the CAS6 protein, thereby preventing the adaptor dimer from being reverse transcribed.

Prior to describing the method in more detail, it is noted that unless the description explicitly indicates something to the contrary, none of the description should be construed as requiring that any of the enzymes (e.g., the ligase, CAS6 protein or reverse transcriptase) is added to the reaction at a particular time. For example, the CAS protein can be added before, ligation, after ligation, or immediately before reverse transcription.

Figure 1:
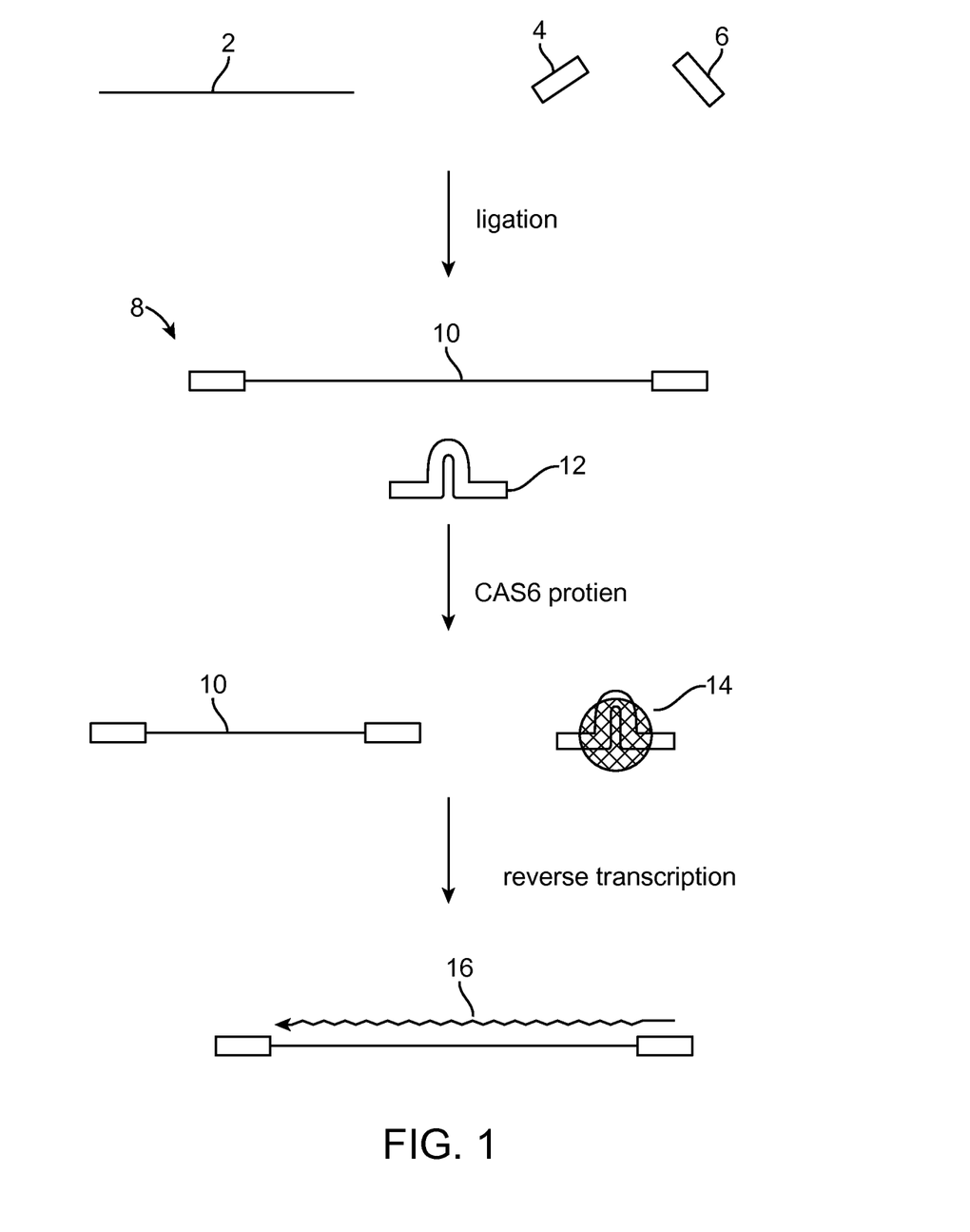
FIG. 1 schematically illustrates some of the principles of the subject method.

Some of the general principles of the method are shown in FIG. 1. With reference to FIG. 1, certain embodiments may involve ligating a target RNA 2 to a pair of adaptors 4 and 6 to produce ligation product 8. Each of the adaptors contains a partial sequence for a CRISPR stem-loop (i.e., one of the adaptors contains 1, 2, 3, 4, 5, 6, 7, 8, 9, or 10 or more nucleotides of the CRISPR stem loop, and the other adaptor contains the remainder of the CRISPR stem loop), and direct ligation of adaptors 4 and 6 to one another produces an adaptor dimer 12 that contains a CRISPR stem-loop. As shown in FIG. 1, ligation products 8 contain an adaptor-ligated target RNA 10 and an adaptor dimer 12 that has the CRISPR stem-loop. The CAS6 protein binds to CRISPR RNA stem-loop of the adaptor dimer to form a complex 14 and, depending on the CAS6 protein used, the adaptor dimer will either be cleaved or the CAS6 protein will bind to the adaptor dimer with high affinity, thereby preventing the adaptor dimer from being reverse transcribed. In certain embodiments, at least the CRISPR stem loop portions of the adaptors 4 and 6 are made from ribonucleotides. In particular cases, one or two bases in the stem and/or loop of the CRISPR step loop may not be a ribonucleotide. Those nucleotides may be deoxyribonucleotides, for example.

In certain embodiments, the method may further comprises contacting the ligation products with a reverse transcriptase, a primer that hybridizes to at least one of the first and second adaptors (or a complement thereof), and nucleotides, thereby reverse transcribing at least part of any adaptor-ligated target RNA that is produced by ligation of the first and second adaptors to the target RNA into cDNA 16. Exemplary reverse transcriptases include but are not limited to murine leukemia virus (MLV) reverse transcriptase, avian myeloblastosis virus (AMV) reverse transcriptase, respiratory syncytial virus (RSV) reverse transcriptase, equine linfectious anemia virus (EIAV) reverse transcriptase, rous-associated virus-2 (RAV2) reverse transcriptase, SUPERSCRIPT II reverse transcriptase, SUPERSCRIPT I reverse transcriptase, THERMOSCRIPT reverse transcriptase and MMLV RNase⁻ reverse transcriptases. The concentration of the reverse transcriptase can vary and optimal concentrations can be determined empirically and depend on the particular reverse transcriptase used. In some embodiments, the reverse transcriptase is at a concentration of between 10-50 units per microliter.

The first and second adaptors may have the same nucleotide sequence or different nucleotide sequences, may be of any length, and in certain case may contain a molecular barcode or one or more site for priming reverse transcription, PCR amplification and/or sequencing, as needed. In particular embodiments, one or more of the adaptors used may contain sequences that are compatible with a next-generation sequencing platform so that the cDNA, once made, can be clonally amplified in vitro, e.g., using emulsion PCR or by bridge PCR, and then sequenced using, e.g., a reversible terminator method (Illumina and Helicos), by pyrosequencing (454) or by sequencing by ligation (SOLiD).

The CAS6 protein used in the method may be a wild-type CAS6 endoribonuclease or a variant of a wild type CAS6 endoribonuclease that retains its ability to bind to, and in certain cases cleave, a corresponding CRISPR stem loop. In certain cases, the CAS6 protein may be at least 80% identical (e.g., at least 85% identical, at least 90% identical, at least 95% identical or at least 98% identical) to the amino acid sequence of a wild-type CAS6 protein. The CAS6 gene family (and corresponding CRISPR sequences) have been reviewed in Haft et al (PLoS Comput Biol. 2005 1: e60), Godde et al (J Mol. Evol. 2006 62:718-29) and Makarova (Biol. Direct 2011 6:38). Exemplary wild-type CAS6 proteins from bacteria and archae include those defined by GI:307568093 (*Pseudomonas aeruginosa*), GI:81355275 (*Zymomonas mobilis*), GI:81637241 (*Pasteurella multocida*), GI:123593404 (*Nitrosococcus oceani*), GI:81725381 (*Vibrio parahaemolyticus*), GI:122471610 (*Photobacterium angustum*), GI:122439729 (*Vibrio alginolyticus*), GI:152996699 (*Marinomonas* sp. MWYL1), GI:160876478 (*Shewanella baltica*), GI:53728896 (*Actinobacillus pleuropneumoniae*) and GI:146328647 (*Dichelobacter nodosus*), as deposited in Genbank, and others can be readily identified by homology searching, either by BLAST or hybridization. Cognate CRISPR sequences can be identified using similar methods. Because the crystal structure of the CAS6/CRISPR complex has been determined (see, e.g., Park et al *Crystal structure of a Cas6 paralogous protein from Pyrococcus furiosus Proteins* 2012 Epub ahead of print; Wang et al *Interaction of the Cas6 riboendonuclease with CRISPR RNAs: recognition and cleavage* Structure. 2011 19: 257-64; and Carter *Cas6 is an endoribonuclease that generates guide RNAs for invader defense in prokaryotes*. Genes Dev. 2008 22:3489-96) and sequences from various species are known, one would be able to make active variants of those proteins/CRISPR sequences without undue effort. In one embodiment, the amino acid sequence of the CAS6 protein is at least 95% identical to the amino acid sequence of the wild-type Csy4 protein from *Pseudomonas aeruginosa*. In certain embodiments, the CRISPR stem loop may have the sequence <u>CUGCC</u>GUAUA<u>GGCAGC</u> (SEQ ID NO:1), or an variant that contains one or two nucleotide substitutions, where the underlined portions of the sequence form the stem loop.

In certain embodiments, the CAS6 protein blocks the adaptor dimer from being reverse transcribed by cleaving the adaptor dimer. In other embodiments, the active site of the CAS6 protein may be inactivated by one or amino acid substitution such that the protein can still bind to the CRISPR stem loop with high affinity (e.g., a Kd of less than 50 nM, less than 5 nM, less than 0.5 nM or less than 100 pM), but not cleave the CRISPR stem loop (see, e.g., Haurwitz et al EMBO J. 2012 [epub ahead of print] and Sternberg et al RNA 2012 18:661-72). In one example, this may be done substituting the amino acid corresponding to the conserved "His29" residue (Sternberg et al RNA 2012 18:661-72) for another amino acid, e.g., an alanine. In these embodiments, the CAS6 protein blocks the adaptor dimer from being reverse transcribed by binding to the adaptor dimer with high affinity.

The ends of the adaptors (e.g., whether the 5' or 3' of an adaptor is blocked or, alternatively whether the 5' or 3' of an adaptor has a phosphate, a hydroxyl, a cyclic phosphate or another group) may be selected based on the ligase used (which may be a eukaryotic tRNA ligase, an rtcB RNA ligase, or a 3'OH RNA ligase, as defined above) and the ends of the target RNA (which may themselves depend on which method wsa used to prepare the target RNA).

In some embodiments, a eukaryotic tRNA ligase may be used. In these embodiments, the adaptor may comprise a 5'-P, a 5'-OH and/or a 3' terminus comprising either a 2'-PO group and 3'-OH group or a 2',3'-cyclic phosphate group. Eukaryotic tRNA ligase have evolved to specifically catalyze the repair and joining of tRNA that has been cut, either deliberately (by excision of a tRNA intron as a normal part of tRNA biosynthesis) or defensively (due to the action of some exogenous ribotoxins). In contrast to bacteriophage T4 RNA ligase, the manner in which eukaryotic tRNA ligase recognizes cleaved tRNA substrates has been shown to be independent of the sequence or structure of tRNA. Instead, the ligation substrate specificity of eukaryotic tRNA ligase depends exclusively on the presence of an unusual nucleotide modification (a 2'PO,3'OH group) at the terminus of the upstream tRNA fragment. Thus, providing eukaryotic tRNA ligase with a synthesized RNA oligonucleotide containing a 2'-PO, 3'-OH group should result in the ligation of this synthetic oligonucleotide to the 5' terminus of any recipient RNA containing a 5'-phosphate group, regardless of its sequence or structure.

A eukaryotic tRNA ligase contains domains that are modular, and the activities may be activated or inactivated depending on the way in which the method is implemented. For example, if the kinase activity of the enzyme is not desired, it may be inactivated by an alteration in the amino acid sequence of the kinase domain of the enzyme. Likewise, if the cyclic phosphodiesterase activity of the enzyme is not desired, it may be inactivated by an alteration in the amino acid sequence of the cyclic phosphodiesterase domain of the enzyme. As noted above, the eukaryotic tRNA ligase used in the method may minimally have a ligase domain having an amino acid sequence that is at least 80% to the amino acid of the ligase domain of a wild type eukaryotic tRNA ligase. In particular embodiments, the ligase domain of the enzyme used may have an amino acid sequence that is at least 85%, at least 90%, at least 95% or up to 100% identical to the amino acid sequence of the ligase domain of a wild type eukayotic tRNA ligase. If the kinase and cyclic phosphodiesterase domains are present, then they may have at least 85%, at least 90%, at least 95% or up to 100% identical to the amino acid sequence of the domains of a wild type eukayotic tRNA ligase. Because these enzymes are modular, the enzyme used may have chimeric sequences from different species. For example, in one embodiment, the enzyme used may have: a) a ligase domain that is at least 80% identical to the ligase domain of a eukaryotic tRNA ligase from a first species and, optionally, b) a cyclic phosphodiesterase domain that is at least 80% identical to the cyclic phosphodiesterase domain of a eukaryotic tRNA ligase from a second species and/or c) a kinase domain that is at least 80% identical to the kinase domain of a eukaryotic tRNA ligase from a third species. Guidance for which amino acids to change in order to inactivate the kinase and/or cyclic phosphodiesterase activities of a eukaryotic tRNA ligase can be obtained from published material about those enzymes, as well as what is known about other kinases and cyclic phosphodiesterases. In particular cases, the ligation may be done in the presence or absence of ATP.

In certain embodiments, the target RNA may be an unfragmented short RNA that comprises a 5' phosphate group and a 3' OH group, e.g., interfering RNA (siRNA), microRNA (miRNA), tiny non-coding RNA (tncRNA), small modulatory RNA (smRNA) or piwi-interacting small RNA (piRNAs). In other embodiments, the target RNA may a fragment of a long RNA molecule, wherein the fragment comprises a 5'-OH group and a 2'-PO group and a 3' OH group, or a 2'-3'-cyclic phosphate group.

In some embodiments, the target RNA may be present in a fragmented RNA sample comprising: i. RNA fragments of long RNA molecules, wherein the fragments comprise a 5'-OH group and a 2'-3'-cyclic phosphate group or a 2'-PO group and a 3' OH group; and ii. unfragmented short RNA molecules that comprise a 5' phosphate group and a 3' OH group. The short RNA molecules naturally exist in the cell as molecules that contain a 5' phosphate group and a 3' OH group. As such, no further modification of those molecules may be necessary. However, in particular cases, the short RNA molecules may or may not be treated with an enzyme, e.g., a kinase, to further ensure that the ends of those molecules contain 5' phosphate group and a 3' OH group. The long RNA molecules, on other hand, may be fragmented to produce fragments containing a 5'-OH group and a 3' terminus having a 2'-3'-cyclic phosphate group.

RNA may be fragmented by exposing an initial RNA sample comprising intact long RNA molecules and short RNA molecules to fragmentation conditions that favor (e.g., maximize) fragmentation of the long RNA molecules relative to fragmentation of the short RNAs molecules. The fragments produced by this method should contain 5'-OH and a 3' terminus having a 2'-3'-cyclic phosphate group. While there are other ways of producing such fragments, one embodiment involves exposing an initial RNA sample (which may contain, for example, total cellular RNA, total RNA that has been depleted for one or more types of RNA (e.g., rRNA and/or tRNA), or mRNA and small RNA, long non-coding RNA and small RNA, for example, although other combinations are contemplated) to a metal ion at a temperature of at least 50° C. for a suitable period of time.

Methods for fragmenting RNA to produce fragments that contain 5'-OH group and a 3' terminus having a 2'-3'-cyclic phosphate group include chemical, enzymatic or thermal fragmentation methods, protocols for which are known (see, e.g., Chandler et al, Appl. Environ. Microbiol. 2003 69:2950-2958, Guschin et al Appl. Environ. Microbiol. 1997 63:2397-2402; Kelly et al, Anal. Biochem. 2002 311:103-118, Liu et al Environ. Microbiol. 2001 3:619-629, Mehlmann et al, Anal. Biochem. 2005 347:316-323, Nguyen Nucleic Acids Res. 2000 28:3904-3909, Proudnikov Nucleic Acids Res. 2006 24:4535-4542, Small et al, Appl. Environ. Microbiol. 2001 67:4708-4716). In one embodiment, the intact RNA may be fragmented using alkali by, e.g., incubation in NaOH (e.g., 50 mM NaOH) at an elevated temperature (e.g., 55° C.) for a period of time (e.g., 10-30 minutes), as described in Liu et al (Applied and Environmental Microbiology, 2007 73: 73-82). In other embodiments, the fragmentation may be metal ion catalyzed in that the intact RNA may be incubated with a metal ion, e.g, an ion of the lanthanide series or a divalent metal ion such as $Mg^{2+}$ or $Zn^{2+}$ (which may be at a concentration of, e.g., 5 mM to 200 mM) at an elevated temperature (e.g, in the range of 50° C. to 95° C.) for a period of time e.g., 1 minute to 1 hr, as described in, e.g, Brown et al (J. Am. Chem. Soc. 2002 124: 7950-7962). For example, RNA may be fragmented by incubation with 10 mM of zinc sulfate ($ZnSO_4$) or zinc chloride ($ZnCl_2$) in 25 mM of Tris-HCl (pH 7.4) at 60° C. for 30 min, as described by Liu, supra. In another case, the RNA may be incubated with 10 mM $ZnCl_2$ in 10 mM Tris-HCl pH 7 for 15 minutes at 70° C. to produce fragments of 60 to 200 bases in length. Incubation of RNA in 40 mM Tris-acetate pH 8.1, 100 mM KOAc and 30 mM MgOA for 20-30 min at 75° C. results in fragments that are generally between 38 and 150 bases in length, as described by Mehlmann et al (Analytical biochemistry 2005 347: 316-323). All of the incubation periods described above may be altered to increase or decrease the lengths of the fragments that are obtained, as desired. The fragmented sample may contain RNA fragments that are, on average, of a length in the range of 30 to 300 nt in length, e.g., 50 to 200 nt in length.

Because fragmentation using the above methods occurs non-specifically at approximately random positions throughout the RNA, the fragmentation on average occurs in longer RNAs on a per molecule basis because the longer RNA molecules contain more potential sites for fragmentation to occur. For example, fragmentation conditions that fragment RNA to fragments of 60 to 200 bases in length should, on average, fragment an RNA molecule of 3 kb in length at approximately 15 to 50 sites without fragmenting a small RNA of approximately 18-31 nucleotides in length. Fragmentation of an RNA sample that contains long RNA molecules and short RNA molecules therefore results in a fragmented sample that contains: a) fragments of long RNA molecules and b) short RNA molecules which are largely intact. The short RNA molecules in the fragmented sample have defined ends in that the nucleotide sequences at the ends of the molecules are known, whereas the fragments of long RNA (because cleavage is not sequence specific) do not have defined ends. The short RNA molecules are generally unfragmented.

A composition of matter produced in accordance with the above method is also provided. In certain embodiments, the composition comprises a first and second adaptors that produce an adaptor dimer that contains a CRISPR stem loop when they are directly ligated together; the adaptor dimer; and a CAS6 protein that recognizes the CRISPR stem loop. In certain embodiments, the composition may further comprise a reverse transcriptase. Other components of the composition may be described in the context of the method section above.

Kits

Also provided by the subject invention are kits for practicing the subject methods, as described above. In certain embodiments, the subject kits contain at least: an RNA ligase, first and second adaptors that produce an adaptor dimer that contains a CRISPR stem loop when they are directly ligated together and a CAS6 protein that recognizes the CRISPR stem loop. The kit may also contain a reverse transcriptase, reagents for isolating RNAs from a cell, and/or reagents for fragmenting RNA etc. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

Aspects of the present teachings can be further understood in light of the following examples, which should not be construed as limiting the scope of the present teachings in any way.

EXAMPLE 1

Figure 2:
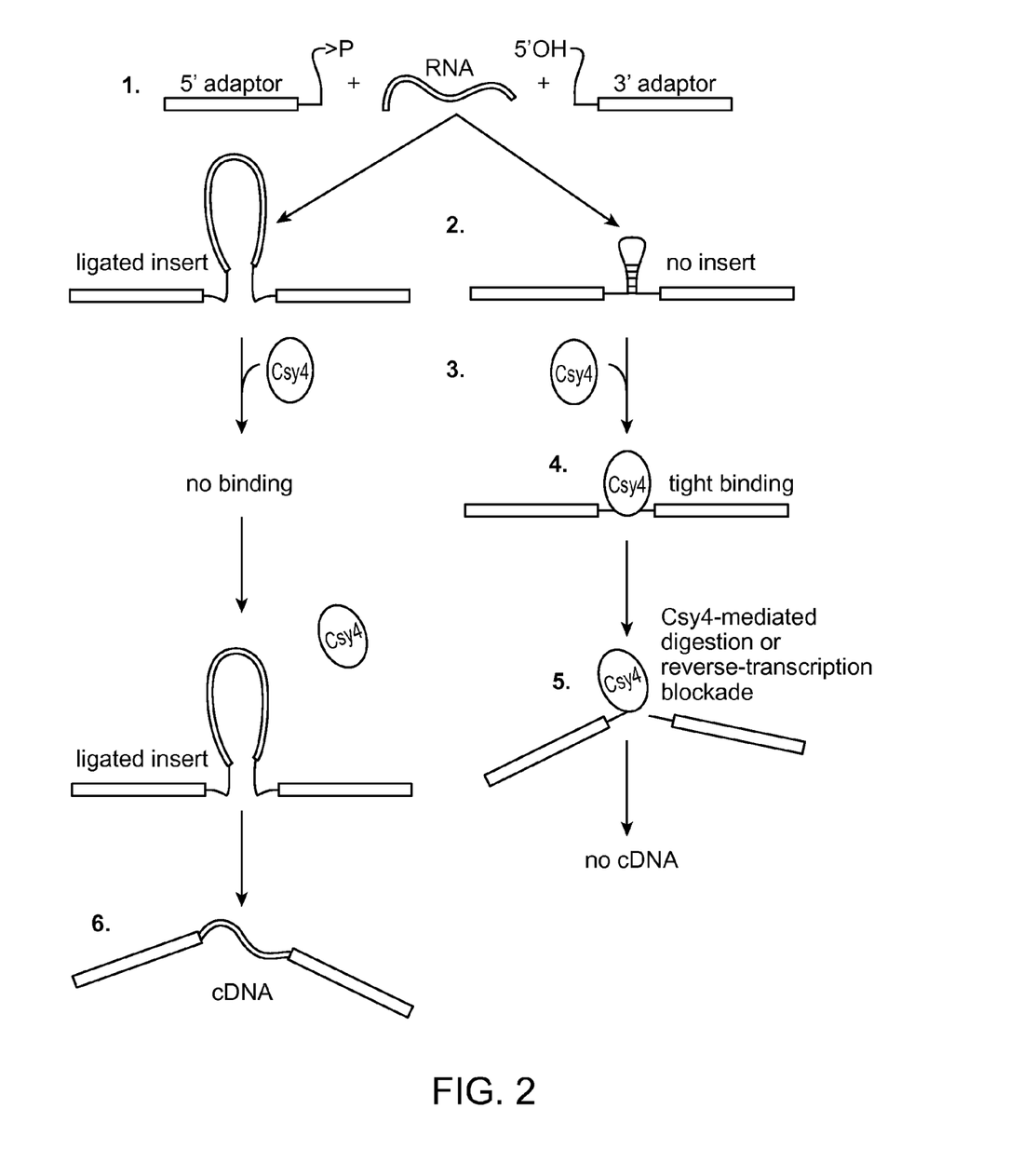
FIG. 2 schematically illustrates an example of a protocol in which the subject method may be employed.

The following protocol, when read in conjunction with FIG. 2, provides a way for making an RNAseq library using eukaryotic tRNA ligase and Csy4/Cas6.

1. 5' and 3' adaptors each containing part of a Csy4/Cas6 stem-loop (thin lines in FIG. 2) are ligated to a pool of RNA, which may contain microRNAs, mRNA fragments, lincRNAs and other RNAs using eukaryotic tRNA ligase, bacteriophage RNA ligase or an RtcB-type RNA ligase.

2. The above ligation should produce RNA inserts to that are ligated to a 5'- and 3'-adaptors (left side of FIG. 2) and also 5'- and 3'-adaptors containing no RNA insert (which are referred to as 'adaptor-dimers', right side of FIG. 2).

3. Recombinant Csy4/Cas6 is added to the ligated products prior to reverse-transcription.

4. Adaptor-dimers are the target of Csy4/Cas6, as a complete and functional Csy4/Cas6 stem-loop will be created when there is no RNA insert. The $K_d$ of Csy4/Cas6 binding to its cognate stem loop is ~50 picomolar. Interrupted Csy4/Cas6 stem-loops (as in the case with an RNA insert) are not recognized by Csy4/Cas6 as these proteins make extensive contacts with both the stem and the loop and any nucleotide substitutions to the stem loop disrupt high-affinity binding.

5. Wild type Csy4/Cas6 contains an endoribonuclease activity that cuts immediately 3' of the stem-loop, which separates the 5' and 3' adaptors from one another. csy4$^{H29A}$ is a mutant Csy4 that lacks the catalytic histidine for endoribonuclease activity, but still retains the same binding affinity for its cognate stem-loop. The csy4$^{H29A}$ mutant can act to sterically hinder reverse-transcription (due to its high affinity for the stem-loop), or imidazole can be added to initiate RNA cleavage in trans.

6. Reverse-transcription will result in cDNA containing adaptors flanking a cDNA insert, whereas no cDNAs will be produced from Csy4/Cas6-bound adaptor-dimers.

3. The method of claim 1, wherein the amino acid sequence of said CAS6 protein is at least 95% identical to the amino acid sequence of the Csy4 protein from *Pseudomonas aeruginosa*.

4. The method of claim 3, wherein said CRISPR stem loop has the sequence CUGCCGUAUAGGCAGC (SEQ ID NO:1).

5. The method of claim 1, wherein said CAS6 protein prevents said adaptor dimer from being reverse transcribed by cleaving said adaptor dimer.

6. The method of claim 1, wherein said CAS6 protein is mutated relative to a wild type sequence so that it is unable to cleave said adaptor dimer, and said CAS6 protein blocks said adaptor dimer from being reverse transcribed by binding to said adaptor dimer with high-affinity.

7. The method of claim 6, wherein said CAS protein has a mutation at His29.

8. The method of claim 1, wherein said first and second adaptors have the same nucleotide sequence.

9. The method of claim 1, wherein said first and second oligonucleotides have different sequences.

10. The method of claim 1, wherein said RNA ligase is eukaryotic tRNA ligase or a bacteriophage RNA ligase.

11. The method of claim 1, wherein said adaptors comprising a 5'-PO, 5'-OH and/or a 3' terminus comprising either a 2'-PO group and 3'-OH group or a 2',3'-cyclic phosphate group.

12. The method of claim 1, wherein said target RNA is an unfragmented short RNA molecule that comprises a 5' phosphate group and a 3' OH group.

13. The method of claim 12, wherein said short RNA molecule is a short interfering RNA (siRNA), microRNA (miRNA), tiny non-coding RNA (tncRNA), small modulatory RNA (smRNA) or piwi-interacting small RNA (piRNAs).

---

---

The invention claimed is:

1. A method of processing a target RNA, comprising:
contacting the products of an RNA ligase-mediated ligation reaction with a CAS6 protein, wherein: (i) said RNA ligase-mediated ligation reaction comprises: a target RNA, an RNA ligase, and first and second adaptors that can ligate together to produce an adaptor dimer that contains a CRISPR stem loop; and (ii) said CAS6 protein recognizes said CRISPR stem loop;
thereby preventing said adaptor dimer from being reverse transcribed.

2. The method of claim 1, wherein the amino acid sequence of said CAS6 protein is at least 80% identical to the amino acid sequence of a wild-type CAS6 protein.

14. The method of claim 1, wherein said target RNA is a fragment of a long RNA molecule, wherein said fragment comprises a 5'-OH group and a 2'-PO group and a 3' OH group or a 2'-3'-cyclic phosphate group.

15. The method of claim 1, further comprising contacting said products with a reverse transcriptase, a primer that hybridizes to an adaptor that hybridizes to at least one of said first and second adaptors, and nucleotides, thereby reverse transcribing at least part of any adaptor-ligated target RNA that are produced by ligation of said first and second adaptors to said target into cDNA.

16. The method of claim 2, wherein said wild-type CAS6 protein is from a species selected from the group consisting of: *Pseudomonas aeruginosa, Zymomonas mobilis, Pasteurella multocida, Nitrosococcus oceani, Vibrio para-*

*haemolyticus, Photobacterium angustum, Vibrio alginolyticus, Marinomonas* sp. MWYL1, *Shewanella baltica, Actinobacillus pleuropneumoniae* and *Dichelobacter nodosus*.

\* \* \* \* \*

UNITED STATES PATENT AND TRADEMARK OFFICE
CERTIFICATE OF CORRECTION

| | | |
|---|---|---|
| PATENT NO. | : 9,102,936 B2 | Page 1 of 1 |
| APPLICATION NO. | : 13/894878 | |
| DATED | : August 11, 2015 | |
| INVENTOR(S) | : Gusti Zeiner et al. | |

It is certified that error appears in the above-identified patent and that said Letters Patent is hereby corrected as shown below:

In the specification,

In column 5, line 30, delete "archebacteria" and insert -- archaebacteria --, therefor.

In column 6, line 8, delete "1084-6)" and insert -- 1084-6). --, therefor.

In column 6, line 28, delete "archae." and insert -- archaea. --, therefor.

In column 8, line 38, delete "linfectious" and insert -- Infectious --, therefor.

In column 9, line 6, delete "archae" and insert -- archaea --, therefor.

In column 9, line 58, delete "wsa" and insert -- was --, therefor.

In column 10, line 29, delete "eukayotic" and insert -- eukaryotic --, therefor.

In column 10, line 33, delete "eukayotic" and insert -- eukaryotic --, therefor.

In column 13, line 30-31, delete "stearically" and insert -- sterically --, therefor.

In the claims,

In column 15, line 1, in claim 16, delete "angustum,Vibrio" and insert -- angustum, Vibrio --, therefor.

Signed and Sealed this
Seventeenth Day of May, 2016

Michelle K. Lee
*Director of the United States Patent and Trademark Office*

SEQUENCE LISTING

<160> NUMBER OF SEQ ID NOS: 1

<210> SEQ ID NO 1
<211> LENGTH: 16
<212> TYPE: RNA
<213> ORGANISM: artificial sequence
<220> FEATURE:
<223> OTHER INFORMATION: synthetic oligonucleotide

<400> SEQUENCE: 1
cugccguaua ggcagc                                                        16